United States Patent [19]
Hartley et al.

[11] 3,957,965
[45] May 18, 1976

[54] SODIUM CHROMOGLYCATE INHALATION MEDICAMENT

[75] Inventors: Philip Saxton Hartley, Kegworth; Stephen Raymond Gunning, East Leake, near Loughborough, both of England

[73] Assignee: Fisons Limited, London, England

[22] Filed: Sept. 27, 1973

[21] Appl. No.: 401,251

Related U.S. Application Data

[60] Division of Ser. No. 158,059, June 29, 1971, Pat. No. 3,860,618, which is a continuation-in-part of Ser. No. 748,937, July 31, 1968, Pat. No. 3,634,582.

[30] Foreign Application Priority Data

Aug. 8, 1967   United Kingdom............... 36270/67

[52] U.S. Cl................................... 424/14; 424/15; 424/283; 260/345.2; 128/208; 259/1 R

[51] Int. Cl.²........................ A61J 3/00; A61J 3/10; A61K 9/00

[58] Field of Search...................... 424/14, 46, 283; 260/345.2

[56]   References Cited
UNITED STATES PATENTS
3,419,578   12/1968   Fitzmaurice et al............. 260/345.2

*Primary Examiner*—V. D. Turner
*Attorney, Agent, or Firm*—Wenderoth, Lind & Ponack

[57]   ABSTRACT

Dosage units comprise a capsule containing a mixture of a solid, finely divided medicament having an effective particle size in the range 0.01 to 10 microns, and a solid, pharmaceutically acceptable, water-soluble carrier having an effective particle size in the range 30 to 80 microns. The compositions are suitable for use in inhalation therapy. The compositions are administered by dispersing the composition into an air stream by subjecting a dosage unit capsule to simultaneous rotation and vibration.

7 Claims, No Drawings

SODIUM CHROMOGLYCATE INHALATION MEDICAMENT

This is a division of application Ser. No. 158,059, filed June 29, 1971, now U.S. Pat. No. 3,860,618, which application is in turn a continuation-in-part of application Ser. No. 748,937, filed July 31, 1968, now U.S. Pat. No. 3,634,582.

The present invention relates to improved pharmaceutical compositions for oral inhalation.

More particularly the invention is concerned with pharmaceutical compositions which are to be dispersed into an air stream by a fluidisation technique which uses the inspiratory action of the inhaler as the principal source of energy. The fluidisation technique is that achieved when powder within a container is subjected to simultaneous rotation and vibration. Such fluidisation is achieved in the dispenser described in French Patent No. 1471722. An example of such a form of device is one which comprises a hollow elongate housing having at both ends thereof one or more passageways adapted to permit the passage of air and having one end thereof adapted for insertion into the mouth and a propeller-like device rotatably mounted in the said housing on a rigid shaft mounted in said housing and co-axial with the longitudinal axis of the housing; said propeller-like device having, on the part thereof furthest from the end of the housing adapted for insertion into the mouth, mounting means adapted to receive a container, such as a gelatine or like capsule for the medicament to be inhaled.

Medicaments for administration by inhalation should be of a controlled particle size in order to achieve maximum penetration into the lungs; a suitable particle size range being 0.01 to 10, usually 1 – 10, microns. However, powders in this particle size range are not readily fluidised by the above technique because of cohesive forces between the individual particles.

It has now been found that such particles may be rendered readily fluidisable and thus suitable for inhalation using such fluidising techniques by mixing the finely divided medicament or pharmaceutically active material with a coarser carrier medium whose particles have sizes falling within a given range.

According to the invention, therefore, there is provided a pharmaceutical powder composition for inhalation which comprises a mixture of a solid finely divided medicament having an effective particle size in the range of 0.01 to 10 microns and a solid pharmaceutically acceptable water soluble carrier having an effective particle size in the range of from 30 to 80 microns. According to a specially preferred embodiment of the invention the composition is substantially free of particles in the effective size range 11 to 29 microns.

For the purpose of the present invention there is no distinction between a single particle of given size and an agglomerate of the same size which is composed of finer individual particles. The term "effective particle size" is therefore used herein and in the claims, where the context permits, to denote the apparent particle size of a body without distinction as to the number of individual particles which go to make up that body. The effective particle sizes quoted herein are those as measured with a Coulter counter.

In measuring particle sizes with a Coulter counter, the sample to be analysed is dispersed in an electrolyte into which dips a glass tube. The glass tube has a hole through the wall thereof with electrodes mounted on either side of the hole in the tube wall. The tube is immersed sufficiently for the hole and electrodes to be submerged in the liquid. The suspension is made to flow through the hole in the glass tube and as each particle passes through the orifice it displaces its own volume of electrolyte, thus changing the resistance across the hole. This change in resistance is converted into a voltage pulse with an amplitude proportional to the particle volume. The pulses are fed to an electronic counter with an adjustable threshold level such that all pulses above the threshold are counted. By setting the threshold level at different values it is possible to determine the number of particles falling within given size ranges and thus the proportion of particles in a sample which fall outside a desired particle size range.

The composition may contain any of a wide variety of medicaments suitable for administration by inhalation, e.g. medicaments intended for alleviation of disorders of the bronchial tract or medicaments administered for systemic action. Particular examples of medicaments which may be employed in the composition of the invention are antianaphylactic agents such as sodium chromoglycate (sodium chromoglycate is the disodium salt of 1,3-bis(2-carboxychromon-5-yloxy)-propan-2-ol) which is useful at a dosage of from 1 to 50 mg in the treatment of allergic asthma, sympathomimetic amines such as isoprenaline or ephedrine, antibiotics such as tetracycline, steroids, enzymes, vitamins, antihistamines and mucolytics such as N-acetyl cysteine. The composition may contain more than one medicament in finely divided form. Thus, a composition may contain, for example a mixture of sodium chromoglycate and isoprenaline sulphate. As stated above, the medicament should be in finely divided form having an effective particle size in the range 0.01 – 10, preferably 1 – 10 microns, and suitably at least 50% by weight of the finely divided medicament is in the effective particle size range 2 – 6 microns. Where the medicament is one of high specific activity, it may be desirable to dilute the medicament with an inert diluent of similar particle size. Such a composition should, of course, also contain a coarser carrier having an effective particle size in the range 30 – 80 microns.

The solid diluent or carrier in the composition will generally be a non-toxic material chemically inert to the medicament but may, if so desired, comprise larger sized particles of the medicament. The carrier has an effective particle size in the range 30 – 80 microns preferably 30 – 70, especially 30 – 60 microns. Examples of water-soluble solid diluents or carriers which may be used in the composition of the invention include dextran, mannitol and, preferably, lactose. A particularly preferred diluent or carrier is crystalline lactose.

As indicated earlier, it is especially desired that the composition be substantially free from particles having an effective size in the range 11 to 29 microns. The term substantially free is used herein and in the claims to denote that the composition contains less than 10%, preferably less than 5%, by weight thereof of particles having effective sizes in the range 11 to 29 microns.

The ratio of medicament or other finely divided material to carrier may vary depending upon the materials used. The optimum ratio will depend upon the nature of the medicament and carrier and the method by which the composition is to be applied. We have found that the use of from 10 – 75% by weight of finely divided material to 90 – 25% by weight of carrier, preferably from 20 to 60% by weight of finely divided materials, e.g. about 35 to 50% by weight of medicament to 65 to 50% by weight of carrier, provides satisfactory results.

The finely divided medicament or other material may be prepared by direct milling down to the desired particle size range and/or particle classification. The particulate carrier may be prepared by grinding the carrier and subsequently separating out the desired fraction by conventional methods, e.g. by air classification and sieving. The surface characteristics of individual particles of both the medicament and carrier may be modified by such conventional techniques as crystallisation, spray drying and precipitation.

The compositions may be prepared from the fine and coarse ingredients by mixing the ingredients together in a mixer, such as a rotating blender, or a planetary or other stirred mixer. The invention thus also provides a method for preparing a composition of the invention which comprises mixing together the finely divided material and the coarse carrier, after comminution and classification of the ingredients if this is necessary. If desired, the surfaces of the particles of medicament and/or diluent and/or carrier may be coated with a pharmaceutically acceptable material, such as stearic acid, or polymers such as polyvinyl pyrolidone. This coating procedure may serve incidentally to give a sustained release action to the medicament.

In addition to the medicament and carrier, the composition may contain other ingredients, such as colouring matter or flavouring agents such as saccharin, which are normally present in inhalant compositions. It is, however, preferred to use the minimum of such other ingredients and that, when present, they should have effective particle sizes in the range 30 – 80 microns.

The compositions according to the invention will generally be put up in gelatine, plastic or other capsules.

There is also provided, therefore, as a further feature of the invention, a dosage unit comprising a gelatine or like capsule containing a pharmaceutical composition comprising a mixture of a solid finely divided medicament having an effective particle size in the range of from 0.1 to 10 microns and a solid pharmaceutically acceptable water soluble carrier having an effective particle size in the range of from 30 to 80 microns.

The amount of composition contained in the capsule will, of course, to some extent depend on the specific activity of the medicament and the desired dosage. However, where possible the capsule suitably contains from 10 to 100 mg. of the composition and for medicaments of high specific activity it may be desirable to dilute the medicament with an inert diluent of similar particle size as described above.

According to a specific feature of the invention, we provide sodium chromoglycate having an effective particle size of from 0.01 to 10 microns, suitably at least 50% by weight of the sodium chromoglycate having an effective particle size of from 2 to 6 microns. Sodium chromoglycate of this effective particle size is useful for mixing with lactose of particle size from 30 to 80 microns in order to produce a composition suitable for inhalation.

In order that the invention may be well understood, the following Examples of compositions according to the invention are given by way of illustration only.

EXAMPLE 1

Commercially available ground crystalline lactose having an effective particle size of from 1 to 100 microns (less than 30% by weight greater than 60 microns, not more than 30% by weight less than 30 microns) was passed through an air classifier, set to remove material having an effective particle size of less than 30 microns. The product from the air classifier contained less than 4% by weight of material of less than 32 microns effective size. This product was then sieved through a sieve having a mesh aperture of 63 microns to produce a lactose product which contained less than 10% by weight of particles with an effective size less than 32 microns and less than 20% by weight with an effective particle size in excess of 62 microns as determined on an Alpine are jet sieve.

The medicament, e,g, sodium chromoglycate, or other material such as lactose which was intended to form the finely divided material was passed through a fluid energy mill in an air stream until the product contained at least 50% by weight of particles in the effective size range 2 – 6 microns as determined on a Coulter counter.

Compositions containing the desired proportions of the coarse and fne materials were mixed together in a planetary mixer and the mixture then passed through a 30 mesh sieve to remove or break up agglomerated particles.

The compositions were then put up in gelatine capsules containing about 40 mg of the composition (capsule approximately one-third full) and the ease of emptying of the composition from the capsule determined. The ease of emptying was assessed by mounting a pierced capsule in the capsule holder of the powder insufflator of French Patent Specification No. 1471722. The insufflator was then mounted in a hole in the side wall of a chamber connected to a bellows. The bellows are designed to suck air through the chamber, and hence the insufflator acting as the air inlet thereinto, at a rate of 1 liter per second. Each suck of the bellows lasted one second.

The capsule was weighed prior to mounting in the insufflator. The bellows were then operated to give seven one second sucks and the capsule reweighed to determine the amount of powder removed is related to the ease of fluidisation of the powder.

The compositions prepared and tested are set out in Table I. By way of comparison a composition containing no coarse diluent was prepared and tested in each case. Those compositions containing the coarse carrier were all found to empty from the capsule at a satisfactory rate, in general from 85 to 90% of the composition, whereas in the absence of the coarse diluent the emptying rates were much lower, about 15% or less, and were unpredictable.

EXAMPLE 2

By way of comparison a further series of compositions were prepared which contained coarse carrier material which possessed an appreciable proportion of particles with an effective size outside the range 30 – 80 microns. The emptying rates for these compositions are set out in Table 2.

From these results it will be seen that the rate of emptying of a capsule, containing a composition which comprises an appreciable proportion of particles whose effective size fell outside the range 30 – 80 microns, was very low and unpredictable thus rendering the administration of such compositions by inhalation unsatisfactory.

Table 1

| Fine materials nature of material and effective particle size. | Parts by weight used | Coarse carrier: nature of material and effective particle size. | Parts by weight used |
| --- | --- | --- | --- |
| Sodium chromoglycate (1–10$\mu$, at least 50% w/w in the range 2–6$\mu$) | 20 | Crystalline lactose (32–63$\mu$) | 19.9 |
| Isoprenaline sulphate (1–10$\mu$, at least 50% w/w in the range 2–6$\mu$) | 0.1 | | |
| Isoprenaline sulphate (1–10$\mu$, at least 50% w/w in the range 2–6$\mu$) | 0.1 | Crystalline lactose (32–63$\mu$) | 19.9 |
| Crystalline lactose (1–10$\mu$, at least 50% w/w in the range 2–6$\mu$) | 20 | | |
| Tetracycline (1–10$\mu$, at least 50% w/w in the range 2–6$\mu$) | 14 | Crystalline lactose (32–63$\mu$) | 26 |
| Penicillin G. (1–10$\mu$, at least 50% w/w in the range 2–6$\mu$) | 10 | Crystalline lactose (32–63$\mu$) | 30 |

Table 2

| Nature of fine material | Effective particle size in microns | Parts by weight used | Nature of coarse material | Effective particle size in microns | Parts by weight used | % w/w of material removed from capsule |
| --- | --- | --- | --- | --- | --- | --- |
| Sodium chromoglycate | 1–10, at least 50% w/w 2–6 | 20 | Crystalline lactose | 32–63 | 20 | 87.2 |
| " | " | 10 | " | Less than 30 | 30 | 0* |
| " | " | 30 | " | " | 10 | 10* |
| " | " | 20 | " | " | 20 | 0* |
| " | " | 0 | " | 1–100 | 40 | Totally unpredictable |
| " | " | 20 | " | 10–30 | 20 | 20* |
| " | " | 20 | " | 10–63 | 20 | 58.6 |

In the above Table the results marked * are unpredictable and many results were at total variance with any general trend which could be assessed. The results of these tests are therefore given as the general trend and not as a mean of the various results obtained.

We claim:

1. A pharmaceutical dosage unit which comprises a pierceable capsule containing a powder composition for inhalation which consists essentially of a heterogeneous particle size readily fluidizable mixture of sodium chromoglycate having an effective particle size in the range 0.01 to 10 microns and a solid pharmaceutically acceptable water-soluble inhalation powder carrier having an effective, coarser particle size in the range of 30 to 80 microns the powder composition containing from 10% to 75% by weight of sodium chromoglycate and from 90% to 25% by weight of said carrier.

2. A dosage unit as claimed in claim 1, wherein the capsule is pierced.

3. A dosage unit according to claim 1 containing from 10 to 100 mg of the said powder composition.

4. A dosage unit according to claim 1 comprising a capsule which is from about one-twelfth to about ten-twelfths full.

5. A dosage unit according to claim 4 comprising a capsule which is about one-third full.

6. A dosage unit according to claim 1 wherein at least 50% by weight of the sodium chromoglycate has an effective particle size of from 2 to 6 microns.

7. A method of administering a pharmaceutical composition, as defined in claim 1, to humans which comprises dispersing the composition into a airstream for inhalation by subjecting a dosage unit as claimed in claim 1 to simultaneous rotation and vibration.

* * * * *